United States Patent [19]
Condon et al.

[11] Patent Number: 6,146,891
[45] Date of Patent: Nov. 14, 2000

[54] METHODS FOR CULTIVATING CELLS AND PROPAGATING VIRUSES

[75] Inventors: Russell G.G. Condon, New Brunswick; Nancy V. Connelly, Union; Andreas Frei, Freehold; Edward Glowacki, Pt. Pleasant, all of N.J.; Vijay Yabannavar, Lafayette, Calif.; Serge Batandolo, Edison, N.J.

[73] Assignee: Schering Corporation, Kenilworth, N.J.

[21] Appl. No.: 09/014,444

[22] Filed: Jan. 28, 1998

Related U.S. Application Data

[60] Provisional application No. 60/035,540, Jan. 31, 1997.
[51] Int. Cl.$^7$ ........................................... C12N 5/00
[52] U.S. Cl. ................. 435/378; 435/41; 435/235.1; 435/239; 435/289.1; 435/325; 435/380; 435/395; 435/403
[58] Field of Search ................. 435/41, 69.1, 235.1, 435/239, 243, 289.1, 325, 378, 380, 395, 403

[56] References Cited

FOREIGN PATENT DOCUMENTS

WO 95/11984  5/1995  WIPO .
WO 95/16772  6/1995  WIPO .
WO 96/22378  7/1996  WIPO .

OTHER PUBLICATIONS

Billig et al., vol. 55, 1984, pp. 67–75.
Chemical Abstract 105:41214, Vretblad et al.
Forestell, et al. Biotech. Bioeng 40: 1039–1044 (1992).
Ohlsen, et al. Cytotechnology 14: 67–80 (1994).
Hu, et al. Biotech Bioeng. 27: 1466–1476.
Huyghe, et al. Human Gene Therapy 6:1403–1416 (1995).
Maiorella et al., Biotech, Bioeng., vol. 37, pp. 121–126 (1991).
Microcarrier Cell Culture—Principles & Methods, pp. 1–128 (Pharmacia).
Microcarrier Cell Culture—Scale–up Methods, pp. 1–27 (Pharmacia).

*Primary Examiner*—Laurie Scheiner
*Attorney, Agent, or Firm*—James M. Gould; David B. Schram

[57] ABSTRACT

This invention relates to methods for the cultivating cells, and in particular to methods for propagating viruses.

24 Claims, 2 Drawing Sheets

METHODS FOR CULTIVATING CELLS AND PROPAGATING VIRUSES

This patent application claims priority under 35 U.S.C §119(e) to provisional application No. 60/035,540 filed Jan. 31, 1997.

BACKGROUND OF THE INVENTION

Many established cell lines are available for a variety of purposes in biotechnology. Some cell lines can be cultivated as single-cell suspensions, but other cell lines do not grow well without a support. The growth of a cell line that requires support is often limited by the surface area available for the cells to grow on, since many cell lines will form only a monocellular layer on the surface. In addition, some cell lines may tend to grow in clumps or aggregates in the absence of a support, which is an undesirable result when they are needed as single-cell suspensions, but more especially when the cells are to be infected with a virus or transformed with a recombinant vector, since the virus or vector may not gain access to the cells within the clump or aggregate. Thus, there can be severe problems in scaling up the cultivation of a cell line, in particular in providing enough surface area for the cells to grow on and/or avoiding clumping of the cells.

Microcarrier technology has been used to cultivate cells in culture. For example, Forestell et al. (*Biotech. Bioeng.* 40: 1039–1044 (1992)) disclosed extended serial subculture of human diploid fibroblasts on microcarriers using a medium supplement that reduced the need of the cultured cells for serum. Furthermore, Ohlson et al. (*Cytotechnology* 14:67–80 (1994)) disclosed the bead to bead transfer of Chinese hamster ovary cells using macroporous gelatin microcarriers. Finally, Hu et al. (*Biotech. Bioeng.* 27: 1466–1476 (1985)) disclosed the serial propagation of mammalian cells on microcarriers using a selection pH trypsinization technique.

However, in view of the problems noted above, there is a need for improvements in methods of cultivating cell lines, in methods of producing viruses for clinical uses, and, in methods of scaling up the production of viruses for larger-scale commercialization. The instant invention meets these needs and more.

SUMMARY OF THE INVENTION

One aspect of the invention is a method for cultivating cells, comprising:
(a) cultivating the cells on a first batch of microcarriers until the cells are substantially confluent;
(b) detaching the cells from the microcarriers without removing the microcarriers from suspension;
(c) Adding a second batch of microcarriers; and
(d) cultivating the cells further.

Another aspect of the invention is a method of detaching cells from a first batch of microcarriers comprises the following steps:
(a) washing the microcarriers and attached cells to remove soluble materials;
(b) contacting the microcarriers and washed cells with a chelating agent;
(c) removing the chelating agent;
(d) trypsinizing the cells for a short period to detach the cells from the microcarriers; and
(e) neutralizing the trypsin by adding protein, wherein (a)–(e) are conducted in a single cultivation vessel.

A further aspect of the invention is a method for the separation of cells from microcarriers on which they have been cultivated but from which they have become detached, comprising introducing an aqueous suspension of cells and microcarriers through an inlet into a separation device, the device comprising
(a) an inlet;
(b) a column;
(c) an outlet for the collection of cells and the aqueous solution; and
(d) a mesh screen;
wherein the microcarriers are retained in suspension by an upward flow in the separation device and are retained in the separation device by a mesh screen, and wherein the cells and aqueous solution are collected through the outlet.

A further aspect of the invention is a system for separating cells from microcarriers on which the cells have been cultivated, the system comprising;
(a) a bioreactor in which the cells were cultivated on the microcarriers;
(b) a flow path from the bioreactor to a separation device;
(c) a separation device comprising
  (I) an inlet;
  (ii) a column;
  (iii) an outlet for the collection of cells and the aqueous solution; and
  (iv) a mesh screen;
  wherein the microcarriers are retained in suspension by the upward flow in the separation device and are retained in the separation device by a mesh screen, and the cells and aqueous solution are collected through the outlet; and
(d) a pump, wherein the pump directs the flow of the aqueous solution from the bioreactor to the outlet.

DETAILED DESCRIPTION OF THE INVENTION

Figure 1:
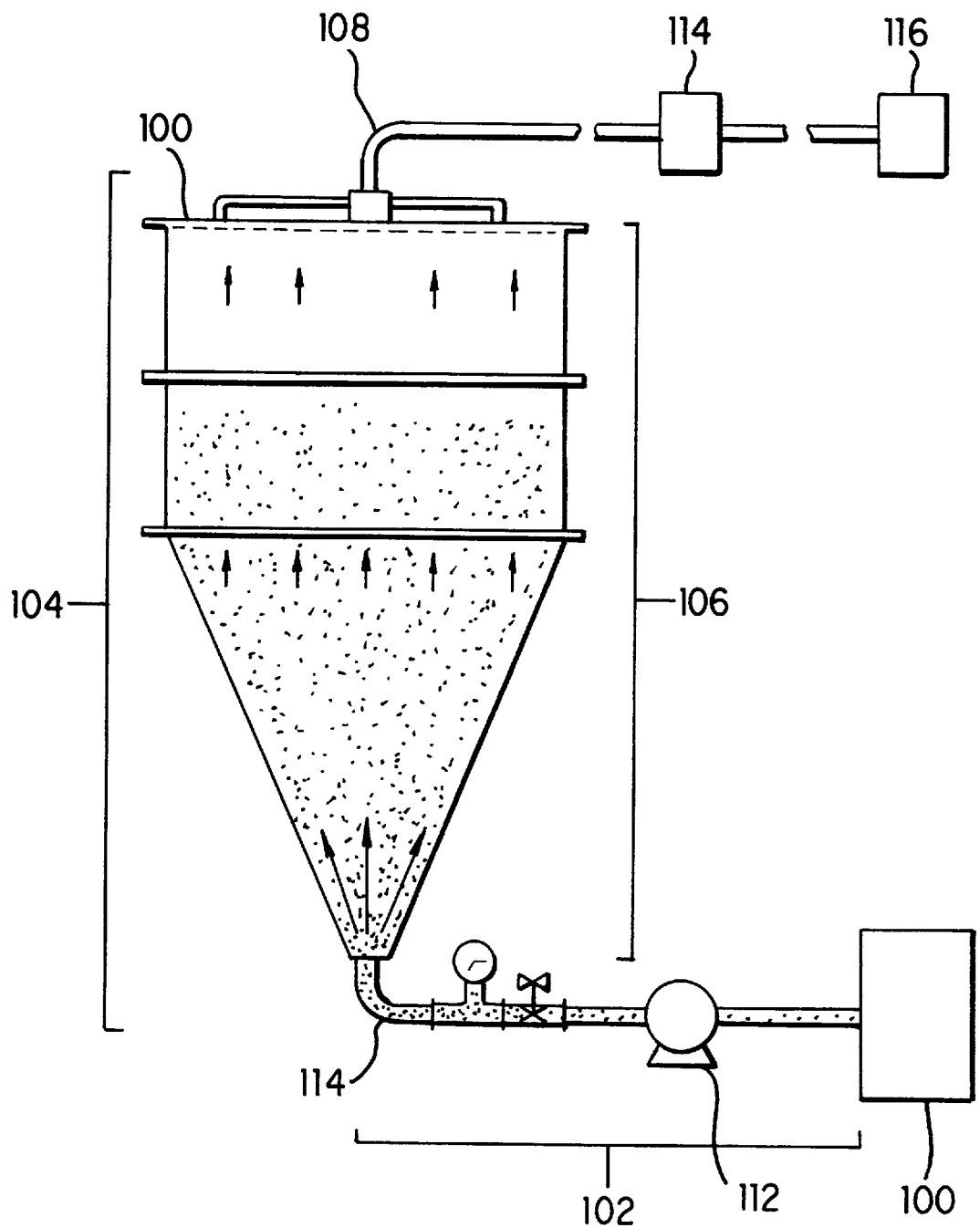
FIG. 1 is a side view of a system according to the present invention used for separating media containing free cells and virus from microcarriers.

The instant invention addresses the large scale cultivation of cells for the propagation of viruses, especially recombinant viruses for gene therapy, vaccine production, and so on. In particular, the instant invention addresses three aspects of large scale cultivation; the use of bead-to-bead transfer of adherent cells to sequentially scale up the number of cells in culture, including the use of trypsin to dissociate cells from microcarriers in bioreactors, the use of fluidized bed-like separation of cells from the beads during harvest, and the use of microfiltration to disrupt cells so as to liberate virus particles.

The term "virus" as used herein includes not only naturally occurring viruses but also recombinant viruses, attenuated viruses, vaccine strains, and so on. Recombinant viruses include but are not limited to viral vectors comprising a heterologous gene. In some embodiments, a helper function(s) for replication of the viruses is provided by the host cell, a helper virus, or a helper plasmid. Representative vectors include but are not limited to those that will infect mammalian cells, especially human cells, and can be derived from viruses such as retroviruses, adenoviruses, adeno-associated viruses, herpes viruses, and avipox viruses. Adenoviral vectors are preferred. Type 2 and type 5 adenoviral vectors are more preferred, with type 5 adenoviral vectors being especially preferred. ACN53 is a recombinant adenovirus type 5 encoding the human wild-type p53 tumor-suppressor protein and is described, for example, in published PCT international patent application WO 95/11984.

As used herein, the term "confluent" indicates that the cells have formed a coherent monocellular layer on the surface (e.g., of the microcarrier), so that virtually all the available surface is used. For example, "confluent" has been defined (R. I. Freshney, *Culture of Animal Cells—A Manual of Basic Techniques,* Wiley-Liss, Inc. New York, N.Y., 1994, p. 363) as the situation where "all cells are in contact all around their periphery with other cells and no available substrate is left uncovered". For purposes of the present invention, the term "substantially confluent" indicates that the cells are in general contact on the surface, even though interstices may remain, such that over about 70%, preferably over about 90%, of the available surface is used. Here, "available surface" means sufficient surface area to accommodate a cell. Thus, small interstices between adjacent cells that cannot accommodate an additional cell do not constitute "available surface".

The cultivation steps in the methods of the present invention can be carried out in a bioreactor or fermentor known in the art of about 1 to 5000 L equipped with appropriate inlets for introducing the cells and microcarriers, sterile oxygen, various media for cultivation, etc.; outlets for removing cells, microcarriers and media; and means for agitating the culture medium in the bioreactor, preferably a spin filter (which also functions as an outlet for media). Exemplary media are disclosed in the art; see, for example, Freshney, *Culture of Animal Cells—A Manual of Basic Techniques,* Wiley-Liss, Inc. New York, N.Y., 1994, pp. 82–100. The bioreactor will also have means for controlling the temperature and preferably means for electronically monitoring and controlling the functions of the bioreactor.

Exemplary microcarriers on which the cells are allowed to grow are known in the art and are preferably specially adapted for the purpose of cell cultivation. General reference is made to the handbook *Microcarrier Cell Culture—Principles & Methods,* published by Pharmacia. However, it should be noted that some cell lines used in the present invention may not adhere strongly to the surfaces of microcarriers; it is well within the ability of one of ordinary skill in the art to determine a suitable combination of cell line, virus (where applicable), microcarrier and culture conditions. The microcarrier preferably has a particle size in the range of about 100 to 250 microns, more preferably in the range of about 130 to 220 microns, and should be composed of a non-toxic material. The median of the sample size preferably falls in these ranges, such that these size ranges are preferably those of at least the middle 90% of the microcarrier sample. In a preferred embodiment, the microcarrier consists of substantially spherical microbeads with a median particle size of about 150 to 200 microns, preferably 170 to 180 microns. The microcarrier surface may be treated to modify cell adhesion, in particular to enhance cell adhesion yet permit proliferation and spreading; thus the microcarriers may be coated, e.g., with collagen. Preferably, the microcarriers are slightly denser than the culture medium, so that gentle agitation will keep them in suspension, whereas simple means such as sedimentation or centrifugation allows their separation. A density of 1.03 to 1.045 g/ml when the microcarriers are equilibrated with a standard solution such as 0.9% NaCl (or with the culture medium) is suitable. The present inventors have found that Pharmacia's Cytodex-3 microcarriers in general will meet these requirements, although the particular requirements that apply for certain cell lines or viruses may require the selection of a particular Cytodex microcarrier.

The cells may be those of any suitable host cell line that is able to replicate itself and in particular support the replication of the virus of interest. A particularly preferred cell line is the human embryonic kidney cell line 293 (ATCC catalog number CRL 1573). These cells do not adhere strongly to all microcarriers, and are preferably used with Pharmacia's Cytodex-3 microcarriers, which are collagen-coated for better cell adhesion. Cytodex-3 microcarriers have a median particle size of about 175 microns with the middle 90% of the sample having a size of about 140 to 210 microns; the density of such microcarriers when equilibrated with 0.9% NaCl is 1.04 g/ml. The cells are preferably cultivated on such a microcarrier in a first step, and then loosened therefrom and transferred to additional microcarriers for a production step.

Stirring can conveniently be effected not only by a paddle at the bottom of the bioreactor but also by a rotating spinfilter, which preferably extends downwards from the top of the bioreactor into the bulk of the medium. The cells and microcarriers can be kept in suspension in the culture by rotation of the spinfilter; the spinfilter may also be equipped with fine orifices that permit the removal of medium without loss of cells. The medium can be removed and replaced simultaneously or alternately; it is frequently convenient to remove a substantial fraction (e.g., up to about 50%) of the medium and then replenish it with the appropriate replacement medium while still removing medium, e.g., through the spinfilter.

Typically, cells are scaled-up from a master working cell bank vial through various sizes of T-flasks, and, preferably, finally to bioreactors. A preferred flask is the CELL FACTORY™ tissue culture flask (CF; NUNC), a specially designed large flask that conveniently has several internal compartments providing a large surface area to which the cells can adhere or attach and on which they can grow. After cultivation until substantially confluent, the cells can be loosened by trypsinization and isolated. The trypsinization is effected for a short period (preferably less than 5 minutes, more preferably about 3 minutes), and the trypsin is then neutralized by the rapid addition of serum in growth medium. If desired, the cells can be centrifuged and the trypsin-containing medium removed before the serum is added. The resulting cell suspension is then typically fed into a seed production bioreactor (typically 20–30 L volume) for further cultivation, and in some embodiments, to a larger production bioreactor (typically 150–180 L volume).

The ratio of volume of the second (larger) bioreactor to the seed bioreactor depends upon the degree to which the cell line is propagated in the first bioreactor, but is typically from 5:1 to 10:1, e.g., in the range of (6–8):1.

Cells are detached from microcarriers by a trypsinization procedure performed in the cultivation vessel, preferably a bioreactor, while the microcarriers are suspended. The spinfilter is utilized to perform medium exchanges to reduce the serum and calcium levels in the medium, which increases the efficiency of the trypsinization while maintaining a constant volume in the bioreactor. Settling steps are avoided which might cause damage to the cells on the microcarriers. The resultant cell/microcarrier suspension can then be transferred to a production bioreactor which is previously charged with culture media and microcarriers.

After the transfer of cell/microcarrier suspension from the seed bioreactor, the production bioreactor (for example, about 200 L) is operated, e.g., at about 37° C. and about pH 7.3. A perfusion of fresh medium during cell propagation can then be performed in order to maintain the lactate concentration below about 1.0 g/L. Cells are typically allowed to grow on the microcarriers for about 4 to 7 days until more than 50% of the microcarriers are completely confluent. Preferably, a virus infection process is then initiated. A vial of 40 to 50 ml viral inoculum, typically containing approximately $1.0 \times 10^{13}$ total viral particles is used to infect the production bioreactor. Virus is allowed to replicate in the production bioreactor for about 3 to 5 days until about the time of maximum virus titer. Typically, more than 90% of cells will have detached from the microcarriers due to cytopathic effects of the virus. The final recombinant adenovirus yield from the production bioreactor is typically about $8.5 \times 10^9$ viral particles/ml. This gives a total yield of viral particles of $1.4 \times 10^{15}$ from each 160-L batch.

In other embodiments of the invention, the production bioreactor is inoculated with cells harvested by trypsinization and then used directly to inoculate the production bioreactor. Typically 8 to 12 CELL FACTORY™ tissue culture flasks are utilized to achieve the overall bioreactor inoculum seeding density of 0.6 to $1 \times 10^5$ cells/ml. The typical virus yield in this method ranges from about 1.7 to $2.6 \times 10^{10}$ viral particles/ml. Therefore, this particular method provides a total virus particle number of about 3 to $4 \times 10^{15}$ from each 160 L batch.

In some embodiments of the invention, a fluidized bed-like process is used to harvest the cells from the bioreactor. Typically, the bioreactor is harvested after about 90% of the cells detach from the microcarriers. Without being limited to any one theory, the cytopathic effect of viral propagation in the host cells appears to be responsible for the cell detachment. In other embodiments, uninfected cells can be detached from microcarriers by the trypsinization method of the instant invention. After the bioreactor is harvested, the broth contains cells, microcarriers and medium. Virus is present in the cells and the medium. Therefore, all of this material is preferably collected for processing. The specific gravity (density) of the microcarriers is similar to that of the cells. Preferably, the microcarriers are kept freely suspended while separating the cells from the beads, as processing steps using sedimentation causes the cells to settle with the microcarriers, which results in recovery losses.

Figure 2:
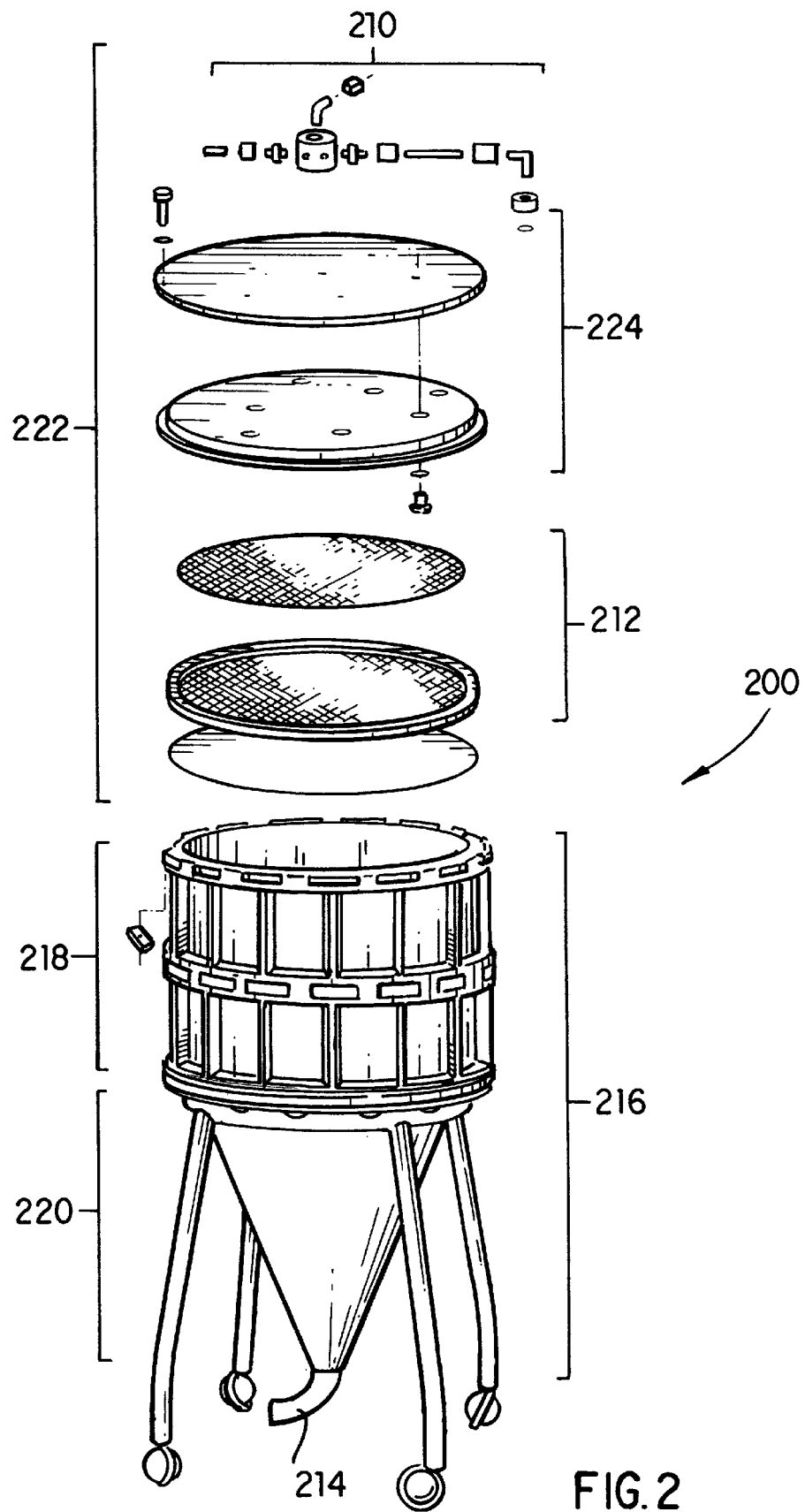
FIG. 2 is an exploded view of a separation device according to the present invention used for separating media containing free cells and virus from microcarriers.

A preferred embodiment of a separation device is provided in FIGS. 1 and 2. In some embodiments of the invention, the separation device is provided as part of a system. An exemplary system is depicted in FIG. 2. The system thus comprises a bioreactor 100 in which the cells are cultivated on microcarriers; a flow path 102 from the bioreactor to the separation device 104; the separation device comprising a column 106; an outlet 108 for the collection of cells and the aqueous solution; and a mesh screen 110. The microcarriers are retained in suspension by an upward flow in the separation device and are retained in the separation device by the mesh screen, and the cells and aqueous solution are collected through the outlet. Also provided in the system is a pump 112, wherein the pump directs the flow of the aqueous solution from the bioreactor to the outlet. In some embodiments, a microfilter 114 and an ultrafilter 116 may be provided as components of the system.

In the embodiment shown in FIG. 1, the separation device typically comprises a column 106, such as a chromatography column, having an inlet 114 through which an aqueous suspension of cells and microcarriers from a bioreactor 100 is introduced into the separation device 104; and at least one outlet 108 for the collection of cells and the aqueous solution; and a mesh screen 110. The microcarriers are retained in suspension in the column by an upward flow in the separation device and are retained in the separation device by a mesh screen, and wherein the cells and aqueous solution are collected through the outlet. The flow rate in the separation device is about 1 to about 3 cm/min. Typically, an upward flow through the column is generated by pumping an aqueous solution, such as the cell suspension or a buffer, through the inlet, wherein the inlet is situated at the bottom of the device and the outlet is situated at the top of the device.

FIG. 2 is an expanded schematic view of a separation device 200, depicting in more detail an outlet assembly 210, a mesh screen assembly 212, an inlet 214, and a column 216 having an upper section 218 and a lower section 220. The lower section typically comprises about 20 to 50%, more preferably about 30%, of the volume of the column and contains the inlet. The lower section is preferably conical, with a preferred angle of about 15 to about 45 degrees.

Thus, the fermentation broth from the bioreactor is pumped into the base of the column. The flow rate is regulated to provide an upward flow sufficient to keep the cells and viral particles suspended in the medium while allowing for the retention of the microcarriers within the separation device. Preferably, the flow rate is approximately 1–2 cm/min since the cells have a specific gravity similar to that of the microcarriers. The clarified broth containing cells and virus passes through the mesh screen on the upper end of the fluidized bed-like column and is collected for microfiltration.

For a 200 L scale device, the lower section of the column preferably is conical. The cone allows for a gradual reduction of the linear velocity of the fermentation broth entering the cone. The fluid velocity of the inlet line is reduced to achieve a reduced linear flow in a uniform distribution across the cross sectional area at the upper end of the cone. The walls of the cone are at an angle which allows the beads that settle on the walls to move downward to the inlet. In this way, these beads are resuspended to avoid entrapment of the cells between the settled beads. The angle of the conical walls is preferably about 30 degrees. Angles less than 15 degrees provide an exceptionally long cone and angles greater than approximately 45 degrees may not disperse the inlet feed effectively. The upper section of the column functions as a zone in which the beads settle at a rate greater than the linear flow rate of the fermentation medium. This section of the column is cylindrical in shape. Within this zone a boundary is formed such that the microcarriers accumulate in the lower region of the column. An end plate assembly 222 (FIG. 2) of the column functions as a collection point for the clarified fermentation media containing cells and virus. This consists of an end plate 224 fitted with a mesh screen assembly. This screen, preferably about 50 to 120 mesh, more preferably about 100 mesh, functions as a second point for removal of the microcarriers.

The above-described embodiment is the preferred embodiment used in the examples herein. The column dimensions and screen mesh may be varied based upon the volume of solution to be processed, the concentration of beads, the particular microcarrier used and the media formulation (e.g., specific gravity of media). A preferred column consists of a bottom cone custom fabricated out of stainless steel to be attached to two Pharmacia KS370 section tubes fitted with a KS370 end assembly to which the vendor screen was replaced with a stainless steel (ss) mesh (preferably about 50 to 120 mesh, more preferably about 100 mesh).

After the cells are collected, they are preferably lysed to liberate additional virus particles. Homogenization or freeze-thawing may be used to liberate the virus particles. In a preferred embodiment of the invention, microfiltration is used to simultaneously lyse virus-containing cells and clarify the broth of cell debris which would otherwise interfere with viral purification. For example, the microfiltration can be performed using a Prostak (Millipore) system with a 0.65 micron, hydrophilic or hydrophobic membrane and at a shear rate of 7000 l/sec. The shear rate is generated by the flow of retentate through the tangential flow channels of the membrane. Therefore, the cross-flow is used not only to prevent the membrane from fouling but can also be used to create enough shear for lysing the cells. The pore size of the filter should be sufficient to allow passage of virus while retaining cell debris. Thus, typically the pore size range is about 0.2–0.65 micron. The shear rate range is typically about 2000 to 10,000 l/sec, more preferably about 7000 l/sec.

Typically, BENZONASE™ endonuclease (American International Chemical, Inc.) is added to the clarified broth to digest cellular nucleic acids, as viral particles can become complexed with cellular nucleic acids. In a preferred embodiment, ultrafiltration using a Pellicon system (Millipore) with a 1 million nominal molecular weight cut-off, Pellicon I-regenerated cellulose membrane is used to concentrate the virus. The ultrafiltration step accomplishes two functions; the virus is concentrated for purification and diafiltration is performed to exchange the buffer so that the virus suspension can be applied directly to a DEAE column. The eluate from the microfilter contains the liberated virus and is preferably concentrated e.g., by ultrafiltration.

Between each cultivation step, the cells can be loosened and stripped from the microcarrier by trypsinization, e.g., by treatment with trypsin. In the present invention it is preferred to remove the serum used in the cultivation, since the serum proteins inhibit the trypsin; removal of the serum therefore allows a smaller amount of trypsin to be used. This is advantageous since addition of a larger amount may cause localized high concentrations of trypsin that could damage the cells. With regard to the next step, $Ca^{++}$ ions are removed since the removal of these ions from the cells tends to loosen the cells and enables one to use less trypsin. Thus, loosening and stripping cells, especially of the human embryonic kidney cell line 293, can conveniently include the following steps:

i) rapidly washing the cells to remove serum and other soluble materials;
(ii) removing Ca++ from the washed cells by adding a chelating agent;
(iii) rapidly removing the chelating agent;
(iv) rapidly adding trypsin;
(v) trypsinizing the cells for a short period of time (preferably ranging from about 3 minutes to about 15 minutes); and
(vi) rapidly neutralizing the trypsin by adding protein.

In step (i) above, the phrase "rapidly washing" means at a constant bioreactor volume perfusing one volume change of medium at a rate of about 1–3 liters per minute, more preferably about 2 liters per minute. In step (iii) above, the phrase "rapidly removing the chelating agent" means at a constant bioreactor volume perfusing one and a half volume changes of medium at a rate of about 1–3 liters per minute, more preferably about 2 liters per minute. In step (iv) above, the phrase "rapidly adding trypsin" means adding the appropriate volume of trypsin solution (typically a 2.5% solution) at a rate of about 1–3 liters per minute, more preferably about 2 liters per minute. In step (vi) above the phrase "rapidly neutralizing the trypsin by adding serum" means adding the appropriate volume of serum at a rate of about 1–3 liters per minute, more preferably about 2 liters per minute.

If the serum is not removed in step (i), then the addition of the necessary large amounts of trypsin can lead to locally high concentrations of trypsin, which can actually damage or even kill the cells rather than simply loosen them. The removal of serum in Step (i) and of $Ca^{++}$ in Step (ii) reduces the amount of trypsin needed in Steps (iv) and (v). To avoid actually damaging or even killing the cells, the treatment with the chelating agent and with the trypsin should preferably be kept short (i.e., long enough to detach the cells from the microcarriers, but preferably not longer). Examples of preferred chelating agents include EDTA (ethylene diamine tetraacetic acid) and EGTA (ethylene-bis (oxyethylene-nitrilo)tetraacetic acid).

The serum is removed by a process of medium exchange; for example, the medium can be pumped off through a spinfilter. Serum-free wash medium is added to replace what was pumped off and the mixture stirred. Alternatively, the addition of serum-free wash medium can be continuous with the removal of medium through the spin-filter. The process is repeated until the serum concentration has been reduced to a sufficiently low level, e.g., less than about 1.0 to 0.2%, preferably about 0.2%. The chelating agent, preferably EDTA, is added in serum-free chelating medium, the mixture again stirred, and the chelating agent pumped off. Alternatively, the addition of the chelating agent in serum-free medium can be continuous with the removal of the medium through the spinfilter.

The trypsin is preferably used in step (v) to provide a concentration in the bioreactor of from about 0.05 to 0.1%, and it is allowed to act on the cells for from 5 to 10 minutes, e.g., preferably a trypsin concentration of about 0.065% for about 8 minutes. Protein, typically in the form of bovine calf serum, is preferably added to the bioreactor in a final concentration of about 10 to 20% to inhibit the trypsin.

Thus the addition of serum in step (vi) not only prepares the cells for further cultivation but also neutralizes residual trypsin. The entire sequence of steps (i)–(vi) can take place in situ in the bioreactor; in some embodiments the suspension of microcarriers and cells can be transferred to a larger bioreactor, where further microcarriers are added for the next step of the cultivation. The cells are allowed to attach to the microcarriers and then are cultivated further. Once they become substantially confluent again (e.g., 3–4 days' cultivation at about 37° C.), they can be put through the next stage, which may for example be harvesting, loosening for a further upstaging, or inoculation with virus. If the cells have been cultivated simply for harvest, then they can be harvested at this stage, e.g., by a repetition of Steps (i) through (vi) above. If they are needed for a further upstaging, then Steps (i)–(vi) above can be repeated. If they have been cultivated for propagation of a virus, the virus can now be inoculated into the medium.

The examples herein serve to illustrate but do not in any way limit the present invention. The selected vectors and hosts and other materials, the concentration of reagents, the temperatures, and the values of other variables are only to exemplify the application of the present invention and are not to be considered limitations thereof.

EXPERIMENTAL EXAMPLES

I. Overview

A. Cell Inoculum Preparation

Each viral fermentation batch is started from a cell line propagated from a vial of 293 cell Manufacturers Working Cell Bank (MWCB). The bioreactors are inoculated with 293 cells (ATCC catalog number CRL 1573) maintained by propagation in T-flasks and CELL FACTORY™ using growth medium (Medium 1), as illustrated in Table 1 below. Each transfer represents a passage. Typically, passage numbers of 4 to 30 are employed for inoculation of a seed bioreactor.

TABLE 1

MEDIA COMPOSITION

| Medium | Purpose | Component Function | Typical Component | Typical Component Range |
|---|---|---|---|---|
| Medium 1 (Growth medium) | Cell Growth | Cell Growth | DMEM Powder[1] | 10–20 g/l |
| | | Cell Growth | Glutamine | 0.1–1.0 g/l |
| | | Cell Growth | Bovine Calf Serum[3] | 5–15% |
| | | Buffer | Sodium Bicarbonate | 2–4 g/l |
| Medium 2 (Serum-free wash medium) | Preparation for trypsinization | Reduce CA** for trypsinization, Later wash | DMEM Powder, Ca** free | 10–20 g/l |
| | | EDTA | | |
| | | Cell Viability | Glutamine | 0.1–1.0 g/l |
| | | Buffer | Sodium Bicarbonate | 2–4 g/l |
| Medium 3 (Serum-free chelating medium) | Preparation for trypsinization | Reduce Ca** for trypsinization | DMEM Powder, Ca** free[2] | 10–20 g/l |
| | | Ca** Chelation | EDTA[4] | 200–400 mg/l |
| | | Cell Viability | Glutamine[5] | 0.1–1.0 g/l |
| | | Buffer | Sodium Bicarbonate | 2–4 g/l |

[1]DMEM powder (available from American Biorganics, Catalog no. D2807): preferably used to provide 4.5 g/L glucose and 0.584 g/L L-glutamine; no sodium bicarbonate and no HEPES.
[2]Ca**-free DMEM powder (available from American Biorganics, Catalog no. D2807403): preferably used to provide 4.5 g/L glucose and 0.584 g/L L-glutamine; no sodium bicarbonate, no calcium chloride and no HEPES.
[3]Bovine calf serum: available from Hyclone, Catalog no. 2151.
[4]EDTA stock solution: 186.1 g/L EDTA and 20 g/L NaOH pellets.
[5]Glutamine stock solution: 29.22 g/L.

To prepare for the transfer of cells from flask to flask during cell expansion, the spent medium is poured off and the cells in the flask are then washed with phosphate-buffered saline (PBS). A trypsin solution is added to the cell monolayer on the flask's surface and the cells are exposed until they detach from the surface. Trypsin action is then largely neutralized by adding growth medium (Medium 1, Table 1) containing serum; complete neutralization is not necessary, since residual trypsin will have low activity. The cells can be recovered by centrifugation and resuspended in fresh growth medium (Medium 1). Table 2 shows the typical volumes are used.

TABLE 2

TYPICAL VOLUMES USED IN TRANSFER OF CELLS

| Flask volume | Surface area | Volume of 0.05% Trypsin Solution | Volume of serum-containing Medium to Inactivate Trypsin | Volume of Medium for Cell Growth |
|---|---|---|---|---|
| T-75 | 75 cm² | 3 ml | 10 ml | 30 ml |
| T-500 | 500 cm² | 25 ml | 50 ml | 200 ml |
| CELL FACTORY ™ | 6000 cm² | 250 ml | 500 ml | 1500 ml |

B. Virus Inoculum Preparation

Virus inocula can be prepared by infecting mature CELL FACTORY™ tissue culture flasks. In this procedure, 293 cells are first propagated from T-flasks to CELL FACTORY™ tissue culture flasks. When CELL FACTORY™ tissue culture flask cultures are mature (typically 80–90% confluent) they are infected with an inoculum from the manufacturer's working virus bank (MWVB). The infected CELL FACTORY™ tissue culture flasks are incubated until the 293 cells detach from their supporting surface. The cells are collected by centrifugation and ruptured by multiple freeze-thaw cycles. After a subsequent centrifugation, the virus is recovered in the supernatant and stored as aliquots at −20° C. or below. This material is the "Virus Inoculum" which is used to infect bioreactors. Optionally, the virus inoculum can also be derived from the bioreactor harvest which is filter-sterilized (see "Production Bioreactor Harvest" below).

C. Seed Bioreactor Preparation and Operation

Preferably, a seed bioreactor is used to prepare the 293 cell inoculum for the production bioreactor. The seed bioreactor is steam-sterilized and charged with a batch of filter-sterilized growth medium (Medium 1, Table 1, above) for the free cell suspension process. For the microcarrier process, however, swelled sterile microcarrier beads (Cytodex 3 or equivalent) are preferably added at this stage.

The seed bioreactor is inoculated with the 293 cells harvested from CELL FACTORY™ tissue culture flasks. The operating conditions are set as shown in Table 3. The pH and dissolved oxygen (DO) are controlled by sparging $CO_2$ and oxygen, respectively. Extra growth medium can be added to the bioreactor by perfusion. Cell growth is monitored by microscopic examination and by measuring the lactate production and glucose consumption. Typically, when the cell density in the suspension culture reaches $1 \times 10^6$ cells/ml in the seed bioreactor, it is ready for inoculating the production bioreactor. However, inoculation requires a few additional steps for the microcarrier process. Typically, when the cells on the microcarriers are >50% confluent, the serum and calcium in the bioreactor medium are washed off using media described in Table 1. Trypsin is then added rapidly, and when the cell detachment reaches typical level, serum is added to inactivate the trypsin. The seed bioreactor contents are now transferred to the production bioreactor.

Optionally, 293 cells harvested from multiple CELL FACTORY™ tissue culture flasks can directly be used as inoculum for a production bioreactor. Typically, 8–12 such cultures are harvested and pooled to provide an inoculum.

TABLE 3

SEED BIOREACTOR OPERATING CONDITIONS

| Variable | Recommended Range | Typical or preferred |
| --- | --- | --- |
| Temperature | 34° C.–39° C. | 37° C. |
| pH | 6.9–7.5 | 7.3 |
| Dissolved Oxygen | >10% | 30% air saturation |
| Pressure | >0.05 bar | 0.1 bar |
| Aeration Overlay | >50 Liters/hour | 180 Liters/hour |
| Agitation | >20 rpm | Initially 50–70 rpm, with optional stepwise increases |
| Spinfilter | >20 rpm | Initially 50–70 rpm, with optional stepwise increases |
| Trypsinization | >25% of microcarriers have confluent cells | >50% of microcarriers have confluent cells |

TABLE 4

PRODUCTION BIOREACTOR OPERATING CONDITIONS

| Variable | Recommended Range | Typical or preferred |
| --- | --- | --- |
| Temperature | 34° C.–39° C. | 37° C. |
| pH | 6.8–7.5<br>6.8–7.6 | 7.3<br>7.4 after virus infection |
| Dissolved Oxygen | >10% | 30% air saturation |
| Pressure | >0.05 bar | 0.1 bar |
| Aeration Overlay | >500 Liters/hour | 2500 Liters/hour |
| Agitation | >20 rpm | 50–70 rpm |
| Spinfilter | >20 rpm | 50–70 rpm |
| Virus infection time | >25% of microcarriers have confluent cells | >50% of microcarriers have confluent cells |
| Harvest time | >50% of microcarriers are empty | >90% of microcarriers are empty |

D. Production Bioreactor Preparation and Operation

The viral production process is exemplified in a 200-L production bioreactor using growth medium (Medium 1, Table 1). In the suspension culture process, filter-sterilized medium is batched into the bioreactor. However, in the microcarrier process, microcarriers are either sterilized in situ in the production bioreactor or autoclaved externally and charged. These microcarriers are then conditioned in the growth medium (Medium 1) prior to inoculation with 293 cells.

The production bioreactor is inoculated with the 293 cells from the seed bioreactor. The operating conditions are set as shown in Table 4. The pH and dissolved oxygen (DO) are controlled by sparging $CO_2$ and oxygen, respectively. Optionally, extra growth medium can be added to the bioreactor by perfusion. Cell growth is monitored by microscopic examination, and by measurement of lactate production and glucose consumption. Cells are allowed to grow to approximately $1 \times 10^6$ cells/ml. The bioreactor is then inoculated with virus. Preferably, a multiplicity of infection (MOI) ratio expressed as the total viral particles per cell of 50:1 to 150:1 is used. Viral titer is typically performed using the Resource Q HPLC assay. Virus is allowed to propagate until the cell viability drops to about 10%.

The type of virus and its action upon the host cells may determine whether it is necessary to detach the host cells from the microcarriers and/or lyse the cells. At about the time of maximum virus titer (frequently when the cells start to detach from the microcarrier and some of which may lyse, so that the virus starts to escape), the incubation can be stopped and the cells and virus can be harvested. Indeed, in the microcarrier process, 80–90% of the cells, sometimes even more than 90%, may detach from the microcarriers. Without being limited to any one theory, the cytopathic effect of viral propagation in the host cells appears to be responsible for cell detachment. Thus, when adenovirus ACN53 is used with 293 cells, the cells start to detach from the microcarriers after 3 or 4 days' cultivation with the virus.

E. Production Bioreactor Harvest

1. Separation of Cells from Microcarrier

At harvest, the bioreactor contents have to be handled differently depending on whether the process uses free suspension or a microcarrier. In the microcarrier process, a fluidized bed column is preferably used to separate the microcarriers from cells and supernatant. An upward flow rate is maintained so as to retain the microcarriers while the cells and supernatant pass through. The fluidized bed is washed with medium or wash buffer to recover most residual cells and virus, and the washings are combined with the cells and supernatant as an eluate. The fluidized bed operation is not required for the free cell suspension process.

The eluate containing cells and virus is further processed in that the cells are lysed by high shear to release virus, and the eluate is then clarified by means of a cross-flow microfiltration. Typically, 0.65 $\mu$m Durapore (Millipore) or equivalent membranes are used. Towards the end of the microfiltration, the retentate is washed with wash buffer to recover the residual virus into the permeate. After microfiltration, the permeate can be optionally treated with a nuclease such as BENZONASE™ endonuclease.

The permeate from the microfiltration is concentrated by ultrafiltration (with a typically 1 million molecular weight cutoff) and a buffer exchange is performed using the wash buffer. The concentrated and diafiltered retentate containing the virus is then passed through a final filter. The resulting filtrate is stored as "Viral Concentrate" in a freezer at −20° C. or below.

2. Composition and Preparation of Media

Table 1 above lists the media used in the preparation of the viral inoculum and in the fermentation process. All these culture media are prepared by first dissolving the dry DMEM powder and other reagents in purified water. After dissolving the dry powders, these media are adjusted to pH 7.2–7.6 with hydrochloric acid. The media are then sterilized by passing through a 0.2 $\mu$m filter into an appropriate storage container. The sterile media are refrigerated below 10° C. and discarded one month after preparation.

Table 5 lists various buffers used in the process.

TABLE 5

BUFFERS USED IN FERMENTATION AND HARVESTING

| Step | Procedure | Component Function | Typical Component | Typical Component Range |
|---|---|---|---|---|
| Cell inoculum preparation in flasks | Wash with PBS prior to trypsinization | Cell Electrolyte Balance | Potassium Chloride | 0.1–0.3 g/l |
| | | Cell Electrolyte Balance | Potassium Phosphate monobasic | 0.1–0.3 g/l |
| | | Ionic Strength | Sodium Chloride | 6–10 g/l |
| | | Buffer | Sodium Phosphate dibasic | 0.5–2 g/l |
| | | Buffer | Sodium Phosphate dibasic heptahydrate | 1–3 g/l |
| Microcarrier preparation | Swell microcarriers with PBS and Tween 80 | Same functions as above + Wetting agent | Same components as above + Tween 80 | Same ranges as above + 0.1–1 ml/l |
| Production bioreactor harvest | Wash fluidized bed, microfilter and ultrafilter retentate with Tris Buffer | Buffer | Tris Base | 4–8 g/l |
| | | Ionic Strength | Sodium Chloride | 7–11 g/l |
| | | Stabilizer | Magnesium Chloride | 0.2–0.6 g/l |
| | | Stabilizer | Sucrose | 16–24 g/l |

Table 6 summarizes the in-process controls during the fermentation and harvesting processes.

TABLE 6

IN-PROCESS CONTROLS

| Step | In-Process Control | Recommended Range |
|---|---|---|
| T-flasks; CELL FACTORY ™: Preparation of inoculum | Microscopic observation | Normal growth and morphology. No contaminants. |
| Seed bioreactor | Microscope observation, measurement of lactate and glucose concentrations, supernatant cell count, sample sterility check. | Normal cell growth and morphology on microcarriers, lactate <1.2 g/L at transer point, no contaminants. |
| Production bioreactor | Microscope observation, measurement of lactate and glucose concentrations, supernatant cell count, sample sterility check. | Normal cell growth and morphology on microcarriers, lactate <1.2 g/L prior to infection, majority of cells detach from microcarriers at harvest, no contaminants. |
| Fluidized bed | Visual observation of fluidized bed, feed pressure and feed flow rate. | Fluidized bed volume to be smaller than total column volume and feed pressure should be below the leak point of the column assembly. |
| Microfiltration | Observation and control of feed flow permeate flow, feed, retentate and transmembrane pressure, retentate temperature | Feed flow rate adjusted to achieve high shear without exceeding a transmembrane pressure of 0.5 bar. Temperature should not exceed 37° C. |
| Ultrafiltration | Observation and control of feed pressure and retentate temperature | Feed pressure should not exceed 1 bar. Temperature should not exceed 37° C. |
| Final filtration | Observation and control of feed pressure | Feed pressure should not exceed 2 bar |

II. Bead to Bead Transfer From Seed Bioreactor to Production Bioreactor

A. 293 Cell Inoculum Preparation for Seed Bioreactor

1. Scale-up from vial to T75 flask

A frozen vial of the 293 cell line containing a total of $2 \times 10^7$ cells was thawed in a 37° C. water bath. The cells were washed with 10 ml of Medium 1. The washed cells were resuspended in a total volume of 30 ml of Medium 1 and placed in a 75 cm² tissue culture flask (T75). The culture was placed in an incubator at 37° C. with a 5% $CO_2$ atmosphere and a humidity level of 100%. This was passage 1 of the culture.

2. Scale-up from T75 Culture to T500 Flask Using Trypsinization

The T75 culture reached a confluency level of 90% in three days. At this time the T75 culture was trypsinized in the following manner. The 30 ml of supernatant medium was removed from the flask. A volume of 10 ml of CMF-PBS (Dulbecco's phosphate buffered saline without calcium chloride and without magnesium chloride) was used to wash the culture surface. The supernatant CMF-PBS was removed from the flask. Two ml of TE (0.05% crude trypsin with 0.53 mM EDTA-4Na) solution was added to the flask. The flask was moved so that the solution covered the entire culture surface. The cells detached from the flask surface within five minutes. Ten ml of Medium 1 was added to the flask immediately after the cells detached from the surface. The cell suspension was centrifuged at 1000 rpm for ten minutes at ambient temperature with the break. The supernatant was removed. The cells were resuspended in five ml of Medium 1. The cell suspension was transferred to a sterile bottle with 200 ml of Medium 1. The 200 ml cell suspension was placed in a 500 cm² tissue culture flask (T500). The liquid in the T500 was allowed to equilibrate between chambers before placement in a horizontal position in the incubator. The culture was placed in an incubator at 37° C. with a 5% $CO_2$ atmosphere and a humidity level of 100%. This was passage 2 of the culture.

3. Scale-up and Passaging of T500 Culture Using Trypsinization

The T500 culture reached a confluency level of 90% in four days. On the fourth day, the T500 culture was trypsinized and scaled-up in the following manner. The supernatant medium was discarded. The culture surface was washed with 25 ml of CMF-PBS. A volume of 25 ml of TE was added to the flask. The flask was moved so that the TE solution covered all three layers of culture surface. The cells detached from the flask surface within five minutes. After the cells detached, 50 ml of Medium 1 was added to the flask. All of the surfaces were contacted with the medium by moving the flask. The resultant cell suspension was poured into a 200 ml conical centrifuge bottle. The cells were pelleted by centrifugation at 1000 rpm for ten minutes at ambient temperature with the brake. The supernatant was discarded. The cells were resuspended in 5 to 15 ml of Medium 1. The cell suspension was placed in 800 ml (200 ml per new T500 flask) of Medium 1. The cell suspension was mixed. A volume of 200 ml of the cell suspension was added to each of four T500 flasks. The liquid level in each flask was allowed to equilibrate between chambers before placement in a horizontal position in the incubator. The split ratio for this passage was 1:4. This was passage 3. The culture was passaged in this manner for passages 4 through 13. At passage 14, four T500 cultures were trypsinized in the manner given above. The cell suspensions were pooled and placed in a bottle containing 1.5 liters of Medium 1. This cell suspension was added to a 6000 $cm^2$ CELL FACTORY™ (CF) tissue culture flask. The liquid level in the CF was allowed to equilibrate between chambers before placement in a horizontal position in the incubator.

4. Scale-up and Passaging of CELL FACTORY™ tissue culture flask Cultures

The CF culture reached an 80% confluency level in three days. The trypsinization was performed in the following manner for passage 15. The 1.5 liters of Medium 1 was drained from the CF culture. The culture surfaces were washed with 500 (+/−100) ml of CMF-PBS. After the wash, 250 (+/−50) ml of TE solution was added to the CF culture. The CF was moved so that the TE solution covered each of the surfaces. After the cells detached from the surface, 500 ml of Medium 1 was added to the CF. The CF was moved so that the Medium 1 contacted each of the surfaces. The resultant cell suspension was aliquotted into four, 250 ml conical centrifuge bottles. The cells were pelleted by centrifugation at 1000 rpm for ten minutes with the brake on. The supernatant medium was discarded from each centrifuge bottle. In each centrifuge bottle, the cells were resuspended in 5 ml of Medium 1. The cells suspensions were pooled into one centrifuge bottle. The three remaining centrifuge bottles were washed with an additional 5–10 ml of Medium 1 which was added to the pooled cell suspension. This cell suspension was split equally among six bottles containing 1.5 liters of Medium 1. Each of the six 1.5 liter cell suspensions was added to a CF. The liquid level of each CF was allowed to equilibrate among the chambers before the CF was placed in a horizontal position in the incubator. The culture was passaged in the same manner for passage 16.

Passaging data are provided in Table 7.

TABLE 7

PASSAGING DATA

| Passage | Culture Time (Days) | Confluency Level at Passage | Source Flask | Recipient Flask |
| --- | --- | --- | --- | --- |
| 1 | 3 | not applicable | vial | T75 |
| 2 | 3 | 90–95% | 1 × T75 | 1 × T500 |
| 3 | 4 | 90–95% | 1 × T500 | 4 × T500 |
| 4 | 3 | 70% | 1 × T500 | 4 × T500 |

TABLE 7-continued

PASSAGING DATA

| Passage | Culture Time (Days) | Confluency Level at Passage | Source Flask | Recipient Flask |
| --- | --- | --- | --- | --- |
| 5 | 4 | 90% | 1 × T500 | 6 × T500 |
| 6 | 4 | 85% | 1 × T500 | 8 × T500 |
| 7 | 3 | 70% | 1 × T500 | 4 × T500 |
| 8 | 4 | 80% | 1 × T500 | 4 × T500 |
| 9 | 4 | 95% | 1 × T500 | 4 × T500 |
| 10 | 3 | 95% | 1 × T500 | 6 × T500 |
| 11 | 3 | 70% | 1 × T500 | 6 × T500 |
| 12 | 4 | 90% | 1 × T500 | 6 × T500 |
| 13 | 4 | 70% | 1 × T500 | 6 × T500 |
| 14 | 4 | 90% | 4 × T500 | 1 CF |
| 15 | 3 | 80% | 1 CF | 6 × CF |
| 16 | 5 | 80% | 1 CF | 6 × CF |

5. Preparation of Cell Inoculum From CELL FACTORY™ tissue culture flask Cultures to the Seed Bioreactor The CF cultures reached an 80% confluency level in five days. Four of the six CF cultures were used to inoculate the seed bioreactor as follows. The 1.5 liters of Medium 1 was drained from the CF culture. The culture surfaces were washed with 500 (+/−100) ml of CMF-PBS. After the wash, 250 (+/−50) ml of TE solution was added to the CF culture. The CF was moved so that the TE solution covered each of the surfaces. Immediately after the cells detached from the surface 500 ml of Medium 1 was added to the CF. The CF was moved so that the Medium 1 contacted each of the surfaces. The resultant cell suspension was aliquotted into four, 250 ml conical centrifuge bottles. The cells were pelleted by centrifugation at 1000 rpm for ten minutes at ambient temperature with the brake on. The supernatant medium was discarded from each centrifuge bottle. In each centrifuge bottle, the cells were resuspended in 5 ml of Medium 1. The cells suspensions were pooled into one centrifuge bottle. The remaining three centrifuge bottles were washed with an additional 5–10 ml of Medium 1 which was added to the pooled cell suspension. The cell suspensions from each of the four centrifuge bottles were then pooled together, yielding a total volume of 50–100 ml. An additional volume of Medium 1 was added to bring the total volume to 1000 ml. This was the cell inoculum. The total amount of cells in the cell inoculum was $2.88 \times 10^9$ total cells and $2.84 \times 10^9$ viable cells. The 1000 ml of cell inoculum was transferred to a sterile Erlenmeyer flask and inoculated into the 30 liter seed bioreactor which contained a total volume of 18 liters of Medium 1 with 66 g of Cytodex 3 microcarriers.

B. Seed Bioreactor

1. Preparation of Cytodex 3 Microcarriers for the 30 L Seed Bioreactor

One batch of 66 grams of Cytodex 3 microcarriers was prepared in the following manner. The 66 grams of Cytodex 3 microcarriers was placed in a five liter, glass, Erlenmeyer flask. Two liters of CMF-PBS with 0.2 ml of Tween 80 was added. The microcarriers were allowed to swell at ambient temperature for five hours and thirty minutes. After this swelling period, the supernatant CMF-PBS was decanted from the flask leaving behind the Cytodex 3 microcarrier slurry. The Cytodex 3 microcarrier slurry was washed with two liters of CMF-PBS then resuspended in CMF-PBS to a total volume of two liters. The batch of Cytodex 3 was autoclaved in the five liter flask at 121° C. for three and a half hours on a liquids cycle. The sterilized Cytodex 3 batch was used the next day for the 30 L Seed Bioreactor.

On the day of the Cytodex 3 addition to the 30 L Seed Bioreactor the following actions were performed. The supernatant CMF-PBS was decanted from the five liter flask. The microcarrier slurry was washed with two liters of Medium 1. After the wash, Medium 1 was added to the flask to a final volume of two liters.

2. Preparation of the 30 L Seed Bioreactor

The 30 L Seed Bioreactor which contained a spinfilter was cleaned and steam sanitized. The bioreactor was sterilized for fifty minutes at 121° C. One day prior to 293 cell inoculation, the 30 L Seed Bioreactor was filled with 18 liters of Medium 1. The two liters containing 66 grams of the Cytodex 3 microcarriers with Medium 1 solution was added to the 30 L Bioreactor. The 30 L Seed Bioreactor operating conditions are listed in Table 8.

TABLE 8

30 L SEED BIOREACTOR OPERATING CONDITIONS

| Operating Condition | Value | Value Range |
|---|---|---|
| pH | 7.3 | 7.1–7.4 |
| Temperature | 37° C. | 35–38° C. |
| Dissolved Oxygen | 30% | 20–140% |
| Bioreactor Pressure | 0.1 bar | 0.05–0.4 bar |
| Aeration Overlay | 180 lph | 100–300 lph |
| Agitation | 70 rpm | 10–100 rpm |
| Spinfilter | 70 rpm | 10–100 rpm |

3. Cultivation of 293 Cells in the 30 L Seed Bioreactor

The 293 cells were propagated on the Cytodex 3 microcarriers for five days. The actual operating conditions in the 30 L Seed Bioreactor during this time period are listed in Table 9.

TABLE 9

OPERATING CONDITIONS IN THE 30 L SEED BIOREACTOR

| Operating Condition | Actual Range | Target |
|---|---|---|
| Temperature | 37–37.1° C. | 37° C. |
| pH | 7.2–7.6 | 7.3 |
| Dissolved Oxygen | 28–100% | 30% |
| Pressure | 0.1 bar | 0.1 bar |
| Aeration Overlay | 200 lph | 200 lph |
| Agitation | 67–94 rpm | 67–94 rpm |
| Spinfilter | 69–87 rpm | 69–87 rpm |

On the fifth day of cultivation, 54% of the microcarrier population contained greater than 50 cells/microcarrier, 38% contained 1–25 cells, 8% contained no cells, and 8% were in aggregates of two microcarriers as determined by examination of a sample under the microscope at 100× magnification. Results are provided in Table 10.

TABLE 10

RESULTS FROM MICROSCOPIC EXAM ON THE FIFTH DAY OF
CULTIVATION OF 293 CELLS ON CYTODEX 3 MICROCARRIERS
IN THE 30L BIOREACTOR
Percent of Total Microcarrier Population

| >50 cells/ microcarrier | 10–50 cells/ microcarrier | 1–10 cells/ microcarrier | empty microcarrier |
|---|---|---|---|
| 54% | 16% | 17% | 7% |

B. Bead to Bead Transfer Procedure

1. Preparation of Cytodex 3 microcarriers for the Production Bioreactor

One batch of 420 grams of Cytodex 3 microcarriers was prepared in the following manner. The 420 grams of Cytodex 3 microcarriers was placed in a fifty liter carboy. A volume of 21.5 liters of CMF-PBS with 2.0 ml of Tween 80 was added. The microcarriers were allowed to swell at ambient temperature for 17 hours. After this swelling period, the supernatant CMF-PBS was removed from the carboy leaving behind the Cytodex 3 microcarrier slurry. The Cytodex 3 microcarrier slurry was washed with 25 liters of CMF-PBS then resuspended in CMF-PBS to a total volume of 20 liters.

The 200 L bioreactor which contained a spinfilter was cleaned and steam sanitized. The 20 liter Cytodex 3 microcarrier slurry was transferred to the bioreactor. Five liters of CMF-PBS was used to wash out the 50 liter carboy and transferred to the bioreactor. The bioreactor was sterilized for 50 minutes at 123° C. The bioreactor was maintained at 4° C. overnight. The next day, 120 liters of Medium 1 was added to the 200 L bioreactor. The microcarrier solution was agitated at 90 rpm for ten minutes in the bioreactor. The volume was brought down to 55 liters by withdrawing liquid through the spinfilter. An additional 110 liters of medium 1 was added to the 200 L bioreactor. The microcarrier solution was agitated at 90 rpm for ten minutes in the bioreactor. The volume was brought down to 55 liters by withdrawing liquid through the spinfilter. Medium 1 was added to the bioreactor to bring the volume to 125 liters. The bioreactor's operating conditions were set according to Table 11.

TABLE 11

BIOREACTOR OPERATING CONDITIONS

| Operating Condition | Target | Actual Range |
|---|---|---|
| Temperature | 37–37.1° C. | 36–38° C. |
| pH | 7.3 | 7.1–7.4 |
| Dissolved Oxygen | 30% | 20–100% |
| Pressure | 0.1 bar | 0.05–0.5 bar |
| Aeration Overlay | 2500 lph | 2500 lph |
| Agitation | 50–90 rpm | 50–90 rpm |
| Spinfilter | 60–100 rpm | 60–100 rpm |

The 200 L production bioreactor was ready to receive the inoculum from the seed bioreactor.

2. Trypsinization of the Seed Bioreactor Culture

On the fifth day of cultivation of the 293 cells on the Cytodex 3 microcarriers, the bead to bead transfer procedure was performed. The serum and calcium levels of the medium in the culture were reduced by perfusing 22 liters of Medium 2 at a rate of 2 liters per minute using the spinfilter with a constant bioreactor volume of 20 liters. Perfusion was continued with 22 liters of Medium 3 at a perfusion rate of 2 liters per minute with a constant bioreactor volume of 20 liters. This reduced the serum and calcium levels further. Medium 3 contained disodium ethylenediaminetetraacetate dihydrate (EDTA) which chelates divalent cations such as magnesium and calcium. A third round of perfusion was performed using 33 liters of Medium 2 which was designed to further reduce the serum and calcium levels and to reduce the concentration of EDTA in the medium. At this point, the medium was withdrawn through the spinfilter to reduce the total culture volume to 15.5 liters. A volume of 480 ml of a 2.5% trypsin solution was added to the bioreactor in one minute. By microscopic observation, eight minutes after the addition of the trypsin solution, 90% of the cells had detached from the microcarriers. At this point, four liters of serum was added to the bioreactor in two and a half minutes to inhibit the action of trypsin and to protect the cells from shear during the transfer procedure to the Production Bioreactor. The trypsinized cells and microcarriers were transferred to the Production Bioreactor by pressure. The transfer was achieved in eight minutes. Immediately after the transfer, five liters of Medium 1 was added to the Seed Bioreactor as a flush and transferred to the Production Bioreactor by pressure. Operating conditions of the seed bioreactor during the bead-bead transfer procedure are provided in Table 12.

TABLE 12

OPERATING CONDITIONS OF THE SEED BIOREACTOR DURING THE BEAD-BEAD TRANSFER PROCEDURE

| Operating Condition | Actual Range | Target |
|---|---|---|
| Temperature | 37° C. | 37° C. |
| pH | 7.2–7.5 | 7.3 |
| Dissolved Oxygen | 28–55% | 30% |
| Pressure | 0.1 bar | 0.1 bar |
| Aeration Overlay | 200 lph | 200 lph |
| Agitation | 89–94 rpm | 89–94 rpm |
| Spinfilter | 86–87 rpm | 86–87 rpm |

C. Cultivation of 293 Cells in the 200 L Production Bioreactor Before Infection

The 293 cells were propagated on the Cytodex 3 microcarriers for six days. The actual operating conditions in the 200 L Production Bioreactor during this time period are listed in Table 13.

TABLE 13

OPERATING CONDITIONS IN THE 200 L PRODUCTION BIOREACTOR

| Operating Condition | Actual Range | Target |
|---|---|---|
| Temperature | 37–37.8° C. | 37° C. |
| pH | 7.2–7.5 | 7.3 |
| Dissolved Oxygen | 43–160% | 30% |
| Pressure | 0.08 bar | 0.1 bar |
| Aeration Overlay | 2500 lph | 2500 lph |
| Agitation | 69–74 rpm | 69–74 rpm |
| Spinfilter | 71–80 rpm | 71–80 rpm |

A total volume of 115 liters of Medium 1 was perfused from days four through six. The rates were as follows; 24 liters was perfused in one hour on day four, 40 liters was perfused in one hour on day five, and 50 liters was perfused in one hour on day six. The oxygen uptake rate measured as the decrease of the dissolved oxygen level (percent of air saturation, % DO) per minute (% DO decrease/min) reached 1.65%/min on day six. Results from microscopic exam on the sixth day of cultivation of 293 cells on Cytodex 3 microcarriers in the 200 L bioreactor are provided in Table 14.

TABLE 14

RESULTS FROM MICROSCOPIC EXAM ON THE SIXTH DAY OF CULTIVATION OF 293 CELLS ON CYTODEX 3 MICROCARRIERS IN THE 200 L BIOREACTOR
Percent of Total Microcarrier Population

| >50 cells/ microcarrier | 10–50 cells/ microcarrier | 1–10 cells/ microcarrier | empty microcarrier |
|---|---|---|---|
| 31% | 23% | 25% | 21% |

D. Infection of the 293 Cells in the 200 L Production Bioreactor

The bioreactor culture was inoculated with virus on day 6. The viral inoculum had been stored frozen at −80° C. A volume of 45 ml of the viral inoculum, 2-2, was thawed in a water bath at 20–25° C. The total amount of virus added to the tank was $1.1 \times 10^{13}$ viral particles as measured by the Resource Q HPLC assay. The viral inoculum was mixed and placed in a bottle with one liter of Medium 4 (293-1-R07 Dulbecco's modified Eagle's medium with L-glutamine and sodium bicarbonate (3.7 g/l)). The viral solution was filtered through a Gelman Maxi Culture Capsule into a sterile five liter addition flask. The viral suspension was added to the 200 L Production Bioreactor with sterile connections made via the tubing welder. Production bioreactor operating conditions after infection are provided in Table 15.

TABLE 15

PRODUCTION BIOREACTOR OPERATING CONDITIONS AFTER INFECTION

| Operating Condition | Actual Range | Target |
|---|---|---|
| Temperature | 37–37.8° C. | 37° C. |
| pH | 7.08–7.23 | 7.4 |
| Dissolved Oxygen | 20–73% | 30% |
| Pressure | 0.08 bar | 0.1 bar |
| Aeration Overlay | 2500 lph | 2500 lph |
| Agitation | 60–74 rpm | 69–74 rpm |
| Spinfilter | 70–80 rpm | 71–80 rpm |

Three days after infection, 89% of the microcarriers did not have attached cells and the oxygen uptake rate measured was 0.53%/min. The total infected cell concentration present in the supernatant broth was $1.0 \times 10^6$ cells/ml. The total volume in the bioreactor was 162 liters. The bioreactor was harvested at this time.

E. Recovery Operations

A volume of 400 liters of the harvest recovery buffer was prepared and filtered through a Pall Ultipor N66 (0.2 micron pore size) and aliquotted into sterile vessels in the following manner. Three aliquots of 210 liters, 130 liters, and 50 liters were prepared. The volume of 210 liters was used for the bioreactor wash and the fluidized bed column operation. The 130 liter aliquot was used during the microfiltration. The 50 liter aliquot was utilized during the ultrafiltration process.

F. Separation of Cells From the Microcarriers Using the Fluidized Bed Column

The fluidized bed was sanitized using a caustic solution (0.1 N sodium hydroxide). A T-fitting was connected to the harvest port of the bioreactor. On one side of the T-fitting, a sanitary hose (15.9 mm id) and valve were connected to the fluidized bed column. A peristaltic pump was placed on this line (Watson Marlow Model 604S). The second side of the T-fitting was connected to a sanitary hose (15.9 mm id) and valve leading to the buffer tank. The outlet of the fluidized bed column, through which the broth containing cells and virus passed, was connected to a tank used as the microfiltration recirculation vessel.

The broth from the bioreactor was passed through the fluidized bed column at a target flow rate of 2–3 liters per minute. The flow rate was controlled with the peristaltic pump. Agitation was maintained in the bioreactor. When the bioreactor volume was less than 100 liters the spin filter was turned off. When the bioreactor volume was less than 30 liters, the agitator was turned off. After the bioreactor contents were processed through the fluidized bed column, the bioreactor was washed with 90 liters of harvest recovery buffer. This wash material was processed through the fluidized bed column. At the end of the process, the microcarriers remained in the fluidized bed column and were discarded. Data are provided in Table 16.

TABLE 16

DATA FROM A FLUIDIZED BED COLUMN OPERATION

| Time (minutes) | Flow Rate (liters per minute) | Volume of Broth processed (liters) | Comments |
|---|---|---|---|
| 0 | 9.8 | 0 | Start |
| 10 | 2.9 | 20 | |
| 60 | 2.9 | 160 | |
| 70 | 2.9 | 160 | Added 90 liters of harvest recovery buffer to bioreactor |
| 100 | 2.9 | 253 | Finish |

G. Microfiltration of the Microcarrier-clarified Broth—Lysing the Infected Cells and BENZONASE™ Endonuclease Treatment The starting material for the microfiltration process was the broth from the fluidized bed column that was clarified of the microcarriers and contained cells and virus. During the microfiltration step, the cells were lysed due to the shear rate used, the broth was clarified of debris larger than 0.65 microns and the residual nucleic acids from the lysed cells was digested by BENZONASE™ endonuclease (e.g., 0.5 million units per 200 L batch), an enzymatic preparation.

The microfiltration unit was a Prostak system (Millipore). It contained a Durapore, 0.65 micron pore size, hydrophilic, membrane (catalog number SK2P446EO) with a surface area of 54 square feet. The feed and retentate lines of the Prostak filter unit were connected to the microfiltration recirculation vessel which contained the microcarrier-clarified broth from the fluidized bed column. A line used to feed the harvest recovery buffer into the microfiltration recirculation vessel was connected. The permeate line from the Prostak unit was connected to the ultrafiltration recirculation vessel. The temperature of the broth was maintained in the range of 25–35° C. When the broth feeding into the Prostak unit was reduced to a volume of 10 to 30 liters in the microfiltration recirculation vessel, 50 liters of the harvest recovery buffer was added to the vessel and the microfiltration continued. This step was repeated once. The microfiltration continued until the volume in the microfiltration recirculation vessel was reduced to 10 to 30 liters. At this time, 0.5 million units of BENZONASE™ endonuclease was added to the clarified in the ultrafiltration recirculation vessel. The contents of the vessel were mixed well and the broth was held for two hours before the ultrafiltration was started. Data are provided in Table 17.

TABLE 17

DATA FROM A MICROFILTRATION OPERATION

| Time | Feed flow rate ($m^3/hr$) | Permeate flowrate ($m^3/hr$) | Inlet pressure (mbar) | Retentate pressure (mbar) | Permeate pressure (mbar) | Broth volume processed (liters) | Comments |
|---|---|---|---|---|---|---|---|
| 0 | 9.6 | 0.17 | 1190 | 273 | 678 | 2 | |
| 4 | 9.6 | 0.16 | 1206 | 278 | 664 | 12 | |
| 20 | 9.6 | 0.16 | 1225 | 258 | 571 | 56 | |
| 36 | 9.6 | 0.15 | 1230 | 249 | 551 | 98 | |
| 50 | 9.6 | 0.16 | 1225 | 244 | 532 | 138 | |
| 63 | 0 | | | | | 176 | Stop and add 50 liters of buffer |
| 71 | 9.6 | 0.18 | 1250 | 268 | 541 | 176 | Start after buffer addition |
| 81 | 9.6 | 0.18 | 1250 | 249 | 532 | 207 | |
| 91 | 0 | 0 | | | | 234 | Stop and add 50 liters of buffer |
| 96 | 9.6 | 0.18 | 1250 | 253 | 522 | 237 | Start after buffer addition |
| 102 | 9.6 | 0.18 | 1264 | 249 | 527 | 258 | |
| 112 | 9.7 | 0.17 | 2284 | 249 | 524 | 286 | |
| 118 | | | | | | 299 | Finish |

H. Ultrafiltration of Broth to Concentrate the Virus with Diafiltration to Perform Buffer Exchange The starting material for the ultrafiltration process in the ultrafiltration recirculation vessel was the BENZONASE™ endonuclease-treated, clarified broth from the microfiltration permeate. The ultrafiltration unit was a Pellicon system (Millipore). It contained a 1 million nominal molecular weight cut-off, Pellicon II-regenerated cellulose membrane (catalog number P2C01MC05) with a surface area of 40 square feet. The feed and retentate lines of the Pellicon unit were connected to the ultrafiltration recirculation vessel. The ultrafiltration permeate line was connected to a waste vessel.

A vessel containing the harvest recovery buffer (50 mM Tris base, 150 mM sodium chloride, 2 mM magnesium chloride hexahydrate, and 2% sucrose) was connected to the ultrafiltration recirculation vessel. When the ultrafiltration retentate volume reached 5 to 10 liters, an addition of 15 liters of the harvest recovery buffer was made and the ultrafiltration was continued. This step was repeated once. The ultrafiltration was continued until the retentate volume was less than 5 to 10 liters. The retentate from the ultrafiltration contained the concentrated virus. The retentate was collected from the Pellicon unit. A flush of 3 to 6 liters of the harvest recovery buffer was used to collect all of the material from Pellicon unit. This flushed material was added to the ultrafilter retentate broth. This was filtered through a Millipore, Durapore, 0.45 micron pore size filter (catalog number CVHL71PP3) into a sterile bag. The material in the sterile bag was stored frozen at −80° C. provided in Table 18.

TABLE 18

DATA FROM AN ULTRAFILTRATION OPERATION

| Time (minutes) | Flow rate (liters per minute) | Inlet pressure (bar) | Retentate pressure (bar) | Permeate pressure (bar) | Comments |
|---|---|---|---|---|---|
| 0 | 16.5 | 0.9 | 3.1 | 0.4 | Start |
| 5 | 16.5 | 0.9 | 3.1 | 0.4 | |
| 39 | 17.3 | 0.9 | 3.1 | 0.4 | |
| 86 | 17.3 | 0.9 | 3.1 | 0.4 | Stop and added buffer |
| 93 | 17.3 | 0.9 | 3.0 | 0.4 | Start after buffer addition |
| 100 | | | | | Stop and added buffer |
| 107 | 15.7 | 0.9 | 3.0 | 0.4 | Start after buffer addition |
| 119 | 15.7 | 0.8 | 3.0 | 0.4 | Flushed unit-finish |

I. General Comments

All 293 cell cultures in T75, T500 and CELL FACTORY™ tissue culture flasks were cultivated in Medium 1 in an incubator at 37° C., 100% humidity and a 5% $CO_2$ atmosphere. All open operations were performed aseptically under a biosafety (laminar flow) hood. Medium fills and additions were performed through a 0.2 micron pore size, PALL Ultipor N66, in-line filter installed on the feed port of the bioreactor which was steam sterilized for 30 minutes at 121° C. All other additions to the bioreactors were performed each using a sterile Erlenmeyer flask with PHARMED™ tubing that was aseptically connected between the bioreactor and the addition flask by a tubing welder. All buffers used in the recovery process were filtered through a 0.2 micron pore size, PALL Ultipor N66, in-line filter (SLK7002NFP) installed on a port of the receiving vessel. Note that for the microfiltration operations either a hydrophilic or hydrophobic membrane can be used.

All publications and patent applications cited herein are incorporated by reference in their entirety to the same extent as if each individual publication or patent application was specifically and individually indicated to be incorporated by reference.

Modifications and variations of this invention will be apparent to those skilled in the art. The specific embodiments described herein are offered by way of example only, and the invention is not to be construed as limited thereby.

What is claimed is:

1. A method for cultivating cells, comprising:
   (a) cultivating the cells on a first batch of microcarriers until the cells are substantially confluent;
   (b) detaching the cells from the microcarriers without removing the microcarriers from suspension and without allowing the microcarriers to settle;
   (c) after step (b), adding a second batch of microcarriers; and
   (d) cultivating the cells further.

2. The method of claim 1 wherein the cells are detached from the first batch of microcarriers by adding trypsin.

3. The method of claim 1 wherein the step of detaching the cells from the first batch of microcarriers comprises the following steps:
   (a) washing the microcarriers and attached cells to remove soluble materials;
   (b) contacting the microcarriers and washed cells with a chelating agent;
   (c) removing the chelating agent;
   (d) trypsinizing the cells for a short period to detach the cells from the microcarriers; and
   (e) neutralizing the trypsin by adding protein, wherein (a)–(e) are conducted in a single cultivation vessel.

4. The method of claim 3 wherein the protein added in (e) is serum.

5. The method of claim 3, wherein the cultivation vessel is a bioreactor.

6. The method of claim 3 wherein the chelating agent is EDTA.

7. The method of claim 3 wherein the trypsin is used in (d) at a concentration of from about 0.05% to about 0.1% for 5 to 10 minutes.

8. The method of claim 3 wherein the trypsin is used in step (d) at a concentration of from about 0.065% to about 0.075% for about 8 minutes.

9. The method of claim 1, wherein a virus capable of infecting the cells is added during (d).

10. The method of claim 9 wherein the virus is added when the cells have become substantially confluent on the microcarriers.

11. The method of claim 9 wherein the virus comprises an adenoviral vector.

12. The method of claim 9 wherein the virus carries a recombinant gene.

13. The method of claim 12 wherein the virus carries a tumor suppressor gene.

14. The method of claim 13 wherein the virus is ACN53.

15. The method of claim 14 wherein the cells are 293 cells.

16. The method of claim 15 wherein the cells are incubated for from 3 to 4 days.

17. The method of claim 1 wherein (c) is carried out in a larger bioreactor than used in (b).

18. The method of claim 1 wherein the microcarriers have a particle size in the range of 100 to 250 microns.

19. The method of claim 1, wherein steps (a) and (b) are carried out in the same vessel.

20. The method of claim 1, wherein steps (a) through (d) are carried out without removing the microcarriers from suspension and without allowing the microcarriers to settle.

21. The method of claim 1, wherein existing culture media is removed during step (b) and new culture media is added.

22. The method of claim 21, wherein the existing culture media is removed through a rotating spinfilter.

23. The method of claim 1, wherein the microcarriers are treated to enhance cell adhesion.

24. The method of claim 22, wherein the microcarriers are coated with collagen.

* * * * *